United States Patent [19]

Büttner et al.

[11] 4,321,204
[45] Mar. 23, 1982

[54] PREPARATION OF CERTAIN 2-METHYL-2,3-DIHYDRO-BENZOFURAN-7-OLS

[75] Inventors: Gerhard Büttner, Pulheim; Karl-Friedrich Christmann, Dormagen; Manfred Lenthe, Odenthal; Udo Allenbach, Cologne, all of Fed. Rep. of Germany

[73] Assignee: Bayer Aktiengesellschaft, Leverkusen, Fed. Rep. of Germany

[21] Appl. No.: 170,443

[22] Filed: Jul. 21, 1980

[30] Foreign Application Priority Data

Aug. 10, 1979 [DE] Fed. Rep. of Germany ....... 2932458

[51] Int. Cl.³ .................................... C07D 307/86
[52] U.S. Cl. ........................................ 260/346.22
[58] Field of Search .................. 260/346.22, 346.73

[56] References Cited

U.S. PATENT DOCUMENTS

3,419,579  12/1968  Towns ........................ 260/346.22
3,876,667  4/1975   Serban et al. ............... 260/346.73

OTHER PUBLICATIONS

Fitzer et al., Technische Chemie, Springer-Verlag, Berlin (1975), p. 346.

*Primary Examiner*—Henry R. Jiles
*Assistant Examiner*—Bernard Dentz
*Attorney, Agent, or Firm*—Sprung, Felfe, Horn, Lynch & Kramer

[57] ABSTRACT

In the preparation of a 7-hydroxycoumaran of the formula

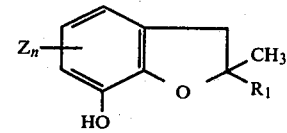

in which
Z is a hydrogen atom or a substituent which is inert under the subsequent reaction conditions,
$R^1$ is a hydrogen atom or a $C_1$ to $C_4$-alkyl radical, and
n is 1, 2 or 3 wherein a pyrocatechol of the formula

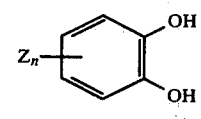

is reacted with an allyl compound of the formula

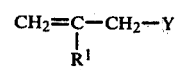

in which
Y is a halogen atom, a $C_1$ to $C_4$-alkyl-sulphonate radical or an aryl-sulphonate radical,
to form the mono-ether of the pyrocatechol in a first stage, and in a second stage, of the pyrocatechol mono-ether formed in the first stage is rearranged to a 3-alkenylpyrocatechol, and in a third stage the 3-alkenyl-pyrocatechol formed in the second stage, is cyclized, the improvement which comprises stages. (b) carrying out the second stage at a pH of about 2-8. Advantageously glycol monomethyl ether is employed as the solvent in all stages and the third stage is carried out with a residence time of about 1-30 minutes and with a narrow residence time spectrum corresponding to a Bodenstein-index 5, optionally in the presence of an iron salt.

8 Claims, No Drawings

PREPARATION OF CERTAIN 2-METHYL-2,3-DIHYDRO-BENZOFURAN-7-OLS

The present invention relates to an unobvious process for the monoalkylation of certain hydroxyphenols and further conversion thereof into hydroxycoumarans.

A number of side reactions can occur in the selective mono-etherification of hydroxyphenols. The undesired formation of the diether significantly reduces the yield of monoether. When reactive alkylating agents, such as optionally substituted alkyl halides, are employed, nuclear-alkylation products can additionally be formed, depending on the solvent used. If the formation of diether is to be suppressed by only partial reaction of the hydroxyphenol, the hydroxyphenol present in excess must be recovered if the process is to be economical. In general, this can be achieved only by an expensive and wasteful extraction with large amounts of solvent. On an industrial scale, a considerable safety risk is associated with distillative separation of the monoether formed because, for example, monoalkenyl ethers of hydroxyphenols in particular rearrange at elevated temperatures to give the isomeric nuclear-substituted hydroxyphenols is a highly exothermic reaction (Claisen rearrangement).

Various processes have been proposed to solve the problems in the preparation of monoethers from hydroxyphenols. It is already known, according to U.S. Pat. No. 2,352,479, that hydroxyphenols, such as, for example, hydroquinone, can be alkylated with alkylating agents, such as, methallyl chloride, in a suspension of $K_2CO_3$ in ethanol at the "reflux temperature." In this reaction, hydroquinone is employed in an excess of 100%.

The Claisen rearrangement is carried out at 225° C. in dimethylaniline as the solvent, and the cyclization to give the hydroxycoumaran is carried out with an excess of pyridine hydrochloride of 100%. A particular disadvantage of the process is the use in the aklylation stage of twice the molar amount, relative to the alkylating agent, of hydroquinone, which cannot be separated off from the monoalkylation product by distillation and must subsequently be recovered by extraction from a dilute aqueous solution. It is necessary to change the solvent for the subsequent Claisen rearrangement. The cyclization to give hydroxycoumarans is carried out with twice the stoichiometric amount of pyridine hydrochloride, although such cyclization reactions require only catalytic amounts of acid.

It is furthermore known (see U.S. Pat. No. 3,474,171), that pyrocatechol can be converted into methallyloxyphenol with methallyl chloride in the presence of equivalent amounts of $K_2CO_3$ and KI in acetone as the diluent if the mixture is heated under reflux for 30 hours. The yield is 45% of theory. Rearrangement and cyclization to give 7-hydroxycoumaran are carried out at 200° to 275° C. without a solvent; no yields are given for these stages. Particular disadvantages for an industrial procedure are, in the alkylation stage, the long reaction times giving a low yield and the use of an equimolar amount of potassium iodide, which is expensive and can be recovered from the salt mixture for renewed use only with high losses. Because of the highly exothermic effect, solvent-free rearrangement of methallyloxyphenol can be carried out only with a great deal of technical effort.

A process for the selective monoalkylation of hydroxyphenols is also described in DOS (German Published Specification) No. 2,451,936 (U.S. Pat. No. 3,927,118). In this process, hydroxyphenols are reacted with alkylating agents and alkaline earth metal hydroxides or alkaline earth metal oxides, as the base, in dipolar aprotic solvents which carry a sulphoxide, sulphone or amide group. The disadvantage of this process is the working up. The reaction products obtained (monoethers and diethers) must first be removed from the reaction mixture by extraction and isolated, large amounts of solvents being separated off. The unreacted hydroxyphenol and the solvent used for the alkylation can then be separated off from the salt residue by a further distillation. For an economic procedure, both the hydroxyphenol employed in an excess of twice the amount and the expensive solvent must be recovered by distillation. However, considerable losses are associated with this recycling.

A process for the preparation of o-methyallyloxyphenol in which pyrocatechol is reacted with methallyl chloride in the presence of alkali metal carbonates or alkali metal bicarbonates in dipolar apriotic solvents and which seeks to overcome the disadvantages of the process according to DOS (German Published Specification) No. 2,451,936, that is to say high excesses of pyrocatechol, is furthermore described in DOS (German Published Specification) No. 2,845,429. However, in this case also, it is not possible to react pyrocatechol completely with a good monoether/diether ratio. On the other hand, separation of the monoether from the chosen dipolar aprotic solvents by distillation presents problems and is difficult because the monoether is unstable to heat and the solvents have high boiling points. An extraction is associated with the disadvantages already described in DOS (German Published Specification) No. 2,451,936.

The present invention now provides a process for the preparation of a 7-hydroxycoumaran of the general formula

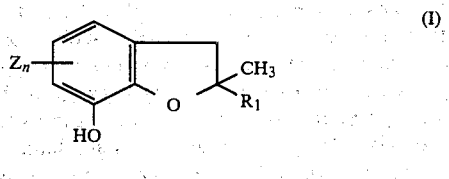

in which
R[1] represents a hydrogen atom or a $C_1$ to $C_4$-alkyl radical,
Z represents a hydrogen atom or a substituent which is stable under the subsequent pesticide-forming reaction conditions and
n is 1, 2 or 3,
by reaction of a pyrocatechol of the general formula

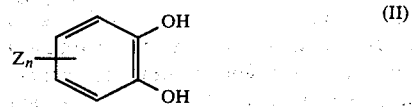

in which
Z and n have the meanings indicated above, with an allyl compound of the general formula

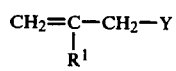

in which
- R[1] represents a hydrogen atom or a $C_1$ to $C_4$ alkyl radical and
- Y represents a halogen atom, a $C_1$ to $C_4$ alkylsulphonate or aryl-sulphonate radical, by mono-etherification of the pyrocatechol in a first stage, and by rearrangement, in a second stage, of the pyrocatechol monoether formed in the first stage, and by cyclization, in a third stage, of the 3-alkenyl-pyrocatechol formed in the second stage, characterized in that the reaction is carried out under one or more of the following reaction conditions (a) a polyhydroxyalkyl ether with at least one OH group can be used as the solvent in individual stages or in all stages, (b) the second stage is carried out at pH about 1–8, (c) the third stage is carried out with short residence times between about 1 and 30 minutes and a narrow residence time spectrum of a Bodenstein-index >5, and (d) the third stage is preferably carried out in the presence of an iron salt.

A particularly preferred embodiment of the present invention is a process comprising all the process conditions (a), (b), (c) and (d), and in which the polyhydroxyalkyl ether with at least one OH group is used as the solvent in all stages.

Further preferred emboiments are processes in which the reaction conditions (a), (b), (c) and (d) are each individually employed.

Preferred substituents Z in formulae (I) and (II) are a hydrogen atom, an alkyl group, a halogen atom, or a nitro group. A $C_1$ to $C_4$ alkyl group and especially a hydrogen atom are particularly preferred.

Preferred substituents Y in formula (III) are a halogen atom, preferably a chlorine atom, or a $C_1$ to $C_4$ alkylsulphonyl, phenylsulphonyl or p-tolylsulphonyl radical.

It is exceptionally surprising that the hydroxyphenol ethers are obtained in high yields with short reaction times in the first stage by choosing polyhydroxyalkyl ethers with at least one free OH group as the diluent. The high yields are achieved without the addition of a co-catalyst. In spite of an excess of alkylating agent, the formation of the corresponding diether is low. A high to quantitative conversion of hydroxyphenol, with high selectivity of the formation of the monoether and simultaneous removal of the water of reaction, is thus possible.

It was furthermore surprising that the 2nd stage proceeds without difficulties and with good yields if it is carried out in a pH range of 2–8 and, preferably, in the same solvent as in the 1st stage.

It was furthermore surprising that a good yield can also be reckoned with in the 3rd stage if this stage is carried out with short residence times (1–30 minutes) and a narrow residence times spectrum, (Bodenstein-index >5) and/or optionally in the presence of iron salts as co-catalysts.

If pyrocatechol and methallyl chloride are used as starting substances, the course of the reaction in stage 1 is illustrated by the following equation:

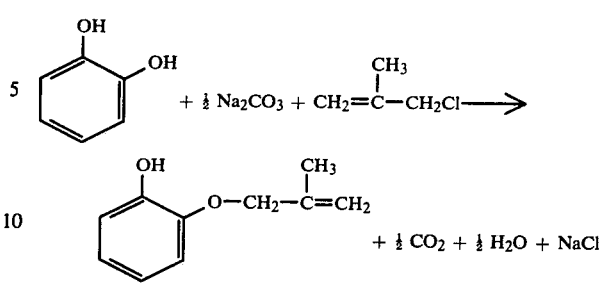

In carrying out the 1st stage of the process according to the invention, 1 mole of hydroxyphenol is generally allowed to react with 1.1–2.5 moles of alkylating agent. A ratio of 1.25–1.8 moles of alkylating agent per mole of hydroxyphenol is preferred. The diluent is generally employed in the ratio of 1.5–5.0 parts by weight per part by weight of hydroxyphenol. The reaction is generally carried out in the presence of a base. Bases which may be mentioned are alkali metal hydroxides, carbonates or bicarbonates or alkaline earth metal hydroxides, carbonates or bicarbonates. Sodium carbonate and sodium bicarbonate are preferred. The reaction can also be carried out in the presence of basic ion exchangers instead of bases.

A ratio of about 2 to 4 kg of diluent per kg of hydroxyphenol is favorable. The alkali metal base is added in a ratio of about 1 to 2 base equivalents per mole of hydroxyphenol. It is advisable to carry out the reaction under a slightly increased pressure of nitrogen and with the addition of a reducing agent, such as sodium dithionite. The reaction is generally carried out at temperatures between 60° and 140° C., preferably between 85° and 125° C.

The polyhydroxyalkyl ethers which have at least one free OH group and may be used as the diluent both in stage 1 and in stages 2 and 3 are preferably glycol monoalkyl ethers with 1 to 4 carbon atoms in the alkyl group of the alkoxy radical; glycol monomethyl ether is particularly preferred.

The water formed in the reaction or imparted with the starting substances is removed during the reaction or thereafter by distillation of an azeotrope.

The salts formed during the reaction can be conveniently separated off by filtration after the reaction.

A continuous procedure for the formation of the monoether is made available, above all at relatively high production rates, by the possibility of removing the water of reaction from the product mixture only when the reaction has ended. In this case, the reaction can be carried out, for example, in a cascade of stirred kettles, into the first stage of which all the reaction partners are introduced. The water of reaction is removed by distillation after the last stage and the salts are removed by filtration.

If pyrocatechol monomethallyl ether is used as the starting substances, the course of the reaction of the 2nd and 3rd stages is illustrated by the following equation:

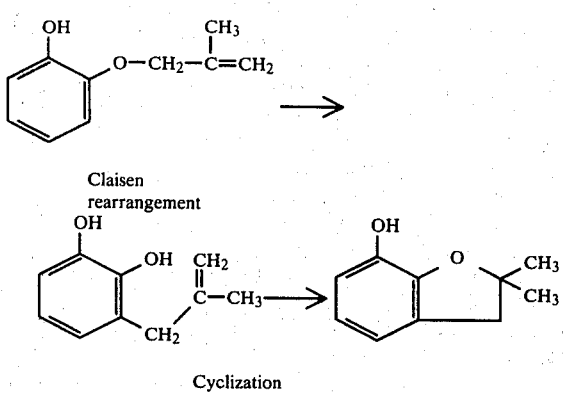

Claisen rearrangement

Cyclization

For carrying out the 2nd stage of the process according to the invention, the alkylating agent employed in excess is distilled off after distilling off the azeotrope. This alkylating agent can be re-used directly in the 1st stage for the preparation of the monoether. The precipitated salts are then separated off and the resulting solution of the monoether is employed in the Claisen rearrangement. However, filtration can also be carried out after removing the water.

The rearrangement can be carried out continuously or discontinuously, generally at temperatures of 140° C.–220° C. and under pressure or under normal pressure. A temperature range of 150°–190° C. is preferred. Because of the relatively highly exothermic effect in the Claisen rearrangement, a continuous procedure is more appropriate.

The 2nd stage is preferably carried out in a pH range of 2–8. The pH value, or accordingly the acid or base content, of the solution of the monoether in the polyhydroxyalkyl ether with at least one free OH group can be determined by a glass electrode or by potentiometric titration by means of 1/10 N NaOH or 1/10 N HCl, after dilution with water. The 2nd stage may be carried out after the 1st stage without changing the diluent.

For carrying out the 3rd stage of the process according to the invention, an acid catalyst (dissolved in the solvent used) is generally added to the solution of the 3-alkenylpyrocatechol from stage 2 and the mixture is heated to temperatures of 120°–230° C., preferably between 140°–220° C. High temperatures and short residence times (5–15 minutes) are preferred. The cyclization to give the 7-hydroxycoumarans can be carried out continuously or discontinuously.

For the procedure, according to the invention, for the 3rd stage, it is essential to carry out the stage with short residence times and a narrow residence time spectrum, (Bodenstein index >5) and optionally in the presence of iron salts as catalysts.

The acid catalyst in stage 3 can be mineral acids, such as HCl, $H_2SO_4$, $H_3PO_4$ or $H_3BO_3$, or strong organic acids, such as sulphonic acids or carboxylic acids. p-Toluenesulphonic acid, which can be metered into the mixture in liquid form in the solvent used, is particularly preferred. Other organic substances which, like methallyl chloride for example, have acid properties can also be used as catalysts. Iron salts, such as $FeCl_3$, exhibit an additional catalytic activity. The concentration of the catalyst is generally 0.2%–2.5% by weight (relative to the solution employed), preferably 0.8%–1.7% by weight.

Stages 1–3 are preferablt carried out continuously or discontinuously under pressure. (Stage 1 can be carried out either under normal pressure or under elevated pressure).

The 7-hydroxycoumaran formed is isolated from the cyclisation reaction directly by distillation of the organic phase. Additional purification steps are not necessary. The solvent thereby obtained in high yields can likewise be re-used directly in the 1st stage.

By removal of the water of reaction, the salts formed during the alkylation reaction separate out quantitatively and can be removed by filtration without problems. It is not necessary to change the solvent for the subsequent reaction to give the hydroxycoumarans. The filtrate from the monoether stage can be employed directly. If stages 2 and 3 are carried out under normal pressure, most of the excess solvent used and excess alkylating agent used are removed during the rearrangement and cyclization.

When working under pressure, the alkylating agent is separated off by distillation before carrying out stages 2 and 3. Most of the solvent remains in the reaction mixture during the Claisen rearrangement and the cyclization and is recovered only during working up of the hydroxycoumaran.

The solvent and alkylating agent recovered are recycled, after working up, to the alkylation stage.

The present invention comprises carrying out the individual separate stages of the process (monoether preparation, Claisen rearrangement of the monoether and cyclization of the rearrangement product), and their combination.

The products, that is to say pyrocatechol monomethallyl ether and 2,2-dimethyl-7-hydroxycoumaran, are known and are used for the preparation of insecticidal (pesticidal) plant protection agents.

EXAMPLE 1

1,150 g of glycol monomethyl ether, 337 g (3 moles) of technical grade pyrocatechol, 178 g (1.68 moles) of anhydrous sodium carbonate and 5 g of sodium dithionite were initially introduced into a 2.5 liter glass reactor on which a short column and a water separator were fitted. A weak stream of $N_2$ was passed through the thoroughly stirred suspension and the latter was heated to an internal temperature of about 110° C. 407 g (4.5 moles) of methallyl chloride (MAC) (in the case of a circulatory procedure, a corresponding amount of recycled MAC) were uniformly metered in via a dropping funnel or a metering pump in the course of 1 hour. A vigorous stream of $CO_2$ already started during heating up, and continued during the subsequent reaction. Throughout the entire reaction time of 4.5 hours (including metering), the water of reaction formed was largely removed. The mixture was cooled to 20° C. and the sodium chloride which had formed was filtered off. The colorless residue on the filter was rinsed twice with a little solvent and the filtrate solvent and wash solvent were combined. The organic phase thus obtained was employed directly for the subsequent Claisen rearrangement and cyclization to give the 7-hydroxycoumaran. According to the gas chromatogram, the organic phase contained 382 g of pyrocatechol monomethallyl ether (boiling point=58° C. under 0.1 mm Hg), which was a yield of 78% of theory. 52 g of diether (boiling point=83° C. under 0.1 mm Hg) were formed, which was 8% of theory. The unreacted pyrocatechol did not interfere with the subsequent reactions. Because of the sensitivity of the monoether and diether to heat, separation of the organic phase into the individual components by distillation was associated with high losses and the danger of an uncontrolled exothermic rearrangement. It was possible to separate off the solvent and the excess of methallyl chloride under a waterpump vacuum.

EXAMPLE 2

337 g (3 moles) of technical grade pyrocatechol, 197 g (1.85 moles) of anhydrous sodium carbonate, 3 g of sodium dithionite and 1,150 g (in the case of circulations, a corresponding amount from the working up operation) of glycol monomethyl ether were initially introduced into a glass reactor analogously to Example 1.

The suspension was heated to 110° C. under a weak stream of $N_2$, and 443 g (4.90 moles) of methallyl chloride were metered in over a period of 45 minutes (discharge of the water of reaction). As soon as the evolution of $CO_2$ subsided (about 4.5 to 5 hours), the mixture was cooled to 20° C. and the precipitate was filtered off and rinsed twice with a little solvent. According to the gas chromatogram, the organic phase thus obtained contained 399 g of pyrocatechol monomethallyl ether (81% of theory) and about 89 of the diether (13.6%). Virtually no pyrocatechol could still be detected. Further processing or working up was effected analogously to Example 1.

EXAMPLE 3

337 g (3 moles) of technical grade pyrocatechol, 178 g (1.68 moles) of anhydrous sodium carbonate and 5 g of sodium dithionite in 950 g of glycol monomethyl ether were initially introduced into a glass reactor as described in Example 1. The mixture was heated to 110° C., while stirring, and 543 g (6 moles) of technical grade methallyl chloride were metered in over a period of 1-1.5 hours. Vigorous evolution of $CO_2$ started immediately. After a total reaction time of 4.5 hours (discharge of water), the evolution of $CO_2$ and separation of water subsided significantly. After cooling, the salt precipitate was filtered off and rinsed. According to the gas chromatogram, the organic phase contained 384 g of pyrocatechol monomethallyl ether (78% of theory), 8 g of 3-methallyl-pyrocatechol (1.6%) and 78 g of the diether (12% of theory). Unreacted pyrocatechol and the diether formed, or its rearrangement products, were separated off by distillation from the 7-hydroxycoumaran formed, after the Claisen rearrangement and cyclization.

EXAMPLE 4

330 g (3 moles) of pyrocatechol, 260 g (3.1 moles) of sodium bicarbonate, 3 g of sodium dithionite and 1,150 g of methylglycol were initially introduced into a glass reactor as described in Example 1, the mixture was heated to 95°-105° C. under a week stream of $N_2$, and 407 g (4.5 moles) of methallyl chloride were uniformly added dropwise in the course of 2 hours.

After a total reaction time of 4.5 hours (discharge of $H_2O$) at 105° C., the mixture was cooled and the dark yellow suspension was filtered. The colorless salt precipitate was filtered off and rinsed. According to the gas chromatogram, the organic phase contained 365 g of pyrocatechol monomethallyl ether (74%) and 63 g of the diether (9.5%). The solvent and unreacted methallyl chloride could be re-used, after working up, in the next batch.

EXAMPLE 5

330 g (3 moles) of pyrocatechol, 350 g (3 moles) of sodium carbonate and 5 g of sodium dithionite in 1,200 g of n-butanol was initially introduced into a glass reactor analogously to Example 1 and 407 g (4.5 moles) of methallyl chloride were metered in at 105° to 110° C., while stirring. The mixture was subsequently stirred for about a further 7 hours at 110° C. and the water discharged is in each case separated off. After cooling, the mixture was filtered and the residue was rinsed with a little n-butanol. According to the gas chromatogram, the organic phase contained 238 g of pyrocatechol monomethallyl ether (48.5% of theory) and 18 g of the diether (2.8% of theory).

EXAMPLE 6

33.0 kg (300 moles) of pyrocatechol (technical grade), 20.7 kg (195 moles) of anhydrous sodium carbonate and 0.33 kg of sodium dithionite were initially introduced into a 270 liter enamel kettle fitted with a column and a water separator, flushing with nitrogen was carried out and, after adding 113.6 kg of glycol monomethyl ether, a suspension was formed, while stirring. After heating the thoroughly stirred suspension to an internal temperature of 110° C., 43.5 kg (480 moles) of methallyl chloride were pumped in with a metering pump at 110° C. in the course of 2 hours. During the addition of the methallyl chloride, the suspension started to boil and water of reaction was removed throughout the entire reaction time of 4.5 hours (including metering) with the distillate, passed over a water separator.

At the end of the reaction time, the unreacted methallyl chloride was distilled off, without reflux and under a pressure of 500 mbars, as an azeotrope with water of reaction which had not been removed. Thereafter, about 40 kg of solvent were distilled off under a pressure of 200 mbars, water of reaction which still remained being virtually completely removed.

The suspension was subsequently cooled to 20° C. and filtered on a suction filter, in order to separate off the solid. The filter cake was washed twice with 10 kg of glycol monomethyl ether each time and the wash filtrate was combined with the filtrate. According to the gas chromatogram, the resulting solution contained 37.3 kg of pyrocatechol monomethallyl ether (76% of theory) and 8.5 kg of pyrocatechol dimethallyl ether (13% of theory).

EXAMPLE 7

33.0 kg (300 moles) of pyrocatechol (technical grade), 20.7 kg (195 moles) of anhydrous sodium carbonate and 0.33 kg of sodium dithionite were initially introduced into a 270 liter enamel kettle, flushing with nitrogen was carried out and, after adding 113.6 kg of glycol monomethyl ether, a suspension was obtained, while stirring. The suspension was heated to 110° C., while stirring thoroughly. During this procedure, carbon dioxide was already liberated and an internal pressure of about 2.8 bars (absolute) built up in the kettle. 43.5 kg (480 moles) of methallyl chloride were subsequently pumped in with a metering pump at an internal temperature of 110° C. in the course of 2 hours, during which the internal pressure in the kettle was kept at 6 bars (absolute) by partial letting down.

After a total reaction time of 4.5 hours (including metering), the mixture was cooled to 20° C. and the pressure was let down. The unreacted methallyl chloride was distilled off under 500 mbars as an azeotrope with the water of reaction.

Thereafter, 40 kg of solvent, which contained the residual water of reaction, were distilled off under 100 mbars. The mixture was cooled to 20° C. and the solid was separated off by filtration on a suction filter.

The filter cake was washed twice with 10 kg of glycol monomethyl ether each time and the filtrate and wash filtrates were combined. According to the gas chromatogram, the resulting solution contained 37.9 kg of pyrocatechol monomethallyl ether (77% of theory) and 6.8 kg of pyrocatechol dimethallyl ether (10% of theory).

EXAMPLE 8

33.0 kg (300 moles) of pyrocatechol (technical grade), 20.7 kg (195 moles) of anhydrous sodium carbonate and 0.33 kg of sodium dithionite were initially introduced into a 270 liter kettle fitted with a column, flushing with nitrogen was carried out and, after adding 113.6 kg of glycol monomethyl ether, a suspension was formed, while stirring. After heating the thoroughly stirred suspension to an internal temperature of 110° C., 43.5 kg (480 moles) of methallyl chloride were pumped in with a metering pump at 110° C. in the course of 2 hours. During this addition, the suspension started to boil and was kept under reflux via the column. At the end of the reaction time of 4.5 hours (including metering), the condensate was removed in order to distil off excess methallyl chloride as the azeotrope with water. Further working up was carried out as described under Example 7. According to the gas chromatogram, the resulting solution contained 38.55 kg of pyrocatechol monomethallyl ether (78% of theory) and 7.4 kg of pyrocatechol dimethallyl ether (11% of theory).

EXAMPLE 9

The organic phase obtained from the monoether preparation was metered continuously into a 3-kettle cascade consisting of 3 glass reactors with a reaction volume of about 0.7 liters and fitted with packed columns, inlet tubes and a lateral overflow or bottom outlet. The 1st reactor was operated at 155° to 160° C. and with a residence time of about 2.5 to 3 hours, methylglycol and methallyl chloride being distilled off over column I. The 2nd reactor was operated at 160° to 180° C. with a residence time of 1 to 2 hours.

The distillates from columns I and II could be reused in the alkylation stage. The 3rd reactor was operated similarly to the 2nd reactor, a small amount of distillate from the 1st column being metered in additionally. It was also possible to meter in a solution of, for example, p-toluenesulphonic acid dissolved in methylglycol, in which case the concentration in the reaction mixture should have been 0.5 to 1.0%.

The 7-hydroxycoumaran formed was isolated by distillation from the reaction solution leaving reactor III. Any high boiling condensation products formed were first separated off via a thin film evaporator. The residual solvent and then the 7-hydroxycoumaran formed (boiling point = 78° C. under 0.3 mm Hg) were subsequently isolated from the distillate in vacuo, over a column.

The yield from the Claisen rearrangement and cyclization together was 65 to 70% of theory.

EXAMPLE 10

The methallyl chloride in the pyrocatechol monomethallyl ether solution (about 5%) was removed by distillation at 65° C. in vacuo, over a column. The solution thus obtained contained 17.6% of pyrocatechol monomethallyl ether and 0.2% of 3-methallylpyrocatechol, which was 17.8% of utilizable products. The term: "utilizable products" was the sum of pyrocatechol monomethallyl ether as the main constituent and 3-methallylpyrocatechol, 3-isobutenylpyrocatechol and any 7-hydroxycoumaran, as secondary constituents.

640 g of this solution per hour were introduced, via a pump, into the 3-stage kettle cascade described in Example 9. The 1st reactor was operated with a residence time of 1.25 hours and at 170° C. and the 2nd reactor was operated with a residence time of 0.75 hour and at 180° C., methylglycol being distilled off, in each case, over columns I and II.

A further 0.75%, relative to the amount flowing through per hour, of p-toluenesulphonic acid, dissolved in methylglycol, were metered into the 3rd reactor, which had a residence time of 0.5 hour and a temperature of 180° C. In addition, a small amount of distillate from the 1st column was introduced. According to analysis by gas chromatography, the reaction solution leaving reactor 3 contained 74 g to 80 g of 7-hydroxycoumaran per hour. This was a yield of 65 to 70% of theory, relative to the utilizable products in the starting solution. Working up was carried out as described in Example 9.

EXAMPLE 11

650 g per hour of the crude solution which originated from the monoether preparation and contained 16.9% of utilizable products were fed continuously, via a pump, into a 1 liter enamel autoclave. The autoclave was operated at 190° C. and with a residence time of 1 hour. According to determination by gas chromatography, the reaction solution leaving the autoclave had a 7-hydroxycoumaran content of 71.4 g/hour to 76.9 g/hour. This was a yield of 65 to 70% of theory. The working up was described in Example 9.

EXAMPLE 12

The crude solution of the monoether was freed from methallyl chloride as indicated in Example 10 and fed continuously, via a pump, into a cascade consisting of 3 one-liter enamel autoclaves. 650 g per hour of the monoether solution, which contained 16.9% of utilizable products, were pumped in. The first two autoclaves were operated at 180° C. and with a total residence time of 1 hour. 0.5% of p-toluenesulphonic acid (3.3 g, dissolved in 6.7 g of methylglycol), relative to the amount flowing through the 3rd reactor per hour, was metered into the 3rd autoclave, which was operated at 160° C. and with a residence time of 1 hour.

According to analysis by gas chromatography, after passage through the 3rd reactor, the reaction solution contained 82.4 g/hour of 7-hydroxycoumaran (75% of theory). Further processing was carried out according to Example 9.

EXAMPLE 13

(Claisen rearrangement in a 3-stage cascade of stirred kettles).

20 liters per hour of a solution of 15% of methallyloxyphenol in glycol monomethyl ether were introduced into a cascade of two enamel kettles, each with a volume of 50 liters, at 180° C. and under 6 bars. According to analysis by gas chromatography, the reaction product flowing out of the cascade contained 12.1% of utilizable products (yield: 80.7%).

EXAMPLE 14

After adding 1.5% of p-toluenesulphonic acid to the solution prepared in Example 13, the mixture was fed into a heated flow tube with an internal diameter of 6 mm and a volume of 490 cm$^3$. A product stream was obtained at a heating agent temperature of 180° C. and with a residence time of 7 minutes, and was worked up according to Example 9. The yield of 7-hydroxycoumaran, relative to the solution employed in this example, was 91%.

EXAMPLE 15

1% of iron-(III) chloride was added to the solution employed in Example 14 and this mixture was reacted under the conditions of Example 14 to give 7-hydroxycoumaran. The yield in this case was 97%, relative to the solution fed into the flow tube. A total yield of 78%, relative to the methallyloxyphenol employed, was thus achieved.

It will be appreciated that the instant specification and examples are set forth by way of illustration and not limitation, and that various modification and changes may be made without departing from the spirit and scope of the present invention.

We claim:

1. In the preparation of a 7-hydroxycoumaran of the formula

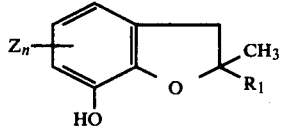

in which

Z is a hydrogen atom or a substituent which is inert under the subsequent reaction conditions, R$^1$ is a hydrogen atom or a C$_1$ to C$_4$-alkyl radical, and n is 1, 2 or 3 wherein a pyrocatechol of the formula

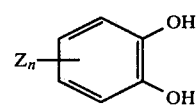

is reacted with an allyl compound of the formula

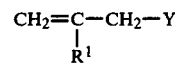

in which

Y is a halogen atom, a C$_1$ to C$_4$-alkyl-sulphonate radical or an aryl-sulphonate radical, to form the mono-ether of the pyrocatechol in a first stage, in a second stage the pyrocatechol mono-ether formed in the first stage is rearranged to a 3-alkenyl-pyrocatechol, and in a third stage the 3-alkenyl-pyrocatechol formed in the second stage is cyclized, the improvement which comprises carrying out the second stage at a pH of about 2-8 and employing a polyhydroxyalkyl ether with at least one OH group as solvent in all three stages.

2. A process according to claim 1, wherein the third stage is carried out in the presence of an iron salt.

3. A process according to claim 1, wherein the third stage is carried out with a residence time of about 1-30 minutes and with a narrow residence time spectrum.

4. A process according to claim 1, wherein Z is a hydrogen atom, an alkyl radical, a halogen atom or a nitro radical.

5. A process according to claim 4, wherein Z is a hydrogen atom or a C$_1$ to C$_4$-alkyl radical.

6. A process according to claim 1, wherein Y is a chlorine atom, or a C$_1$ to C$_4$-alkylsulphonyl, phenylsulphonyl or p-tolylsulphonyl radical.

7. A process according to claim 1, wherein the polyhydroxyalkyl ether with at least one OH group is glycol monomethyl ether.

8. A process according to claim 3, in which

Y is a chlorine atom, or a C$_1$ to C$_4$-alkylsulphonyl, phenylsulphonyl or p-tolylsulphonyl radical, and Z is a hydrogen atom or a C$_1$ to C$_4$-alkyl radical, a solvent consisting essentially of glycol monomethyl ether is employed in all three stages and the third stage is carried out in the presence of an iron salt.

* * * * *